(12) United States Patent
Dewey et al.

(10) Patent No.: US 11,364,124 B2
(45) Date of Patent: Jun. 21, 2022

(54) BUILD-PLATE WITH INTEGRALLY-FORMED SPINAL IMPLANT CONSTRUCTS AND CORRESPONDING METHOD FOR MANUFACTURING SPINAL IMPLANTS

(71) Applicant: Warsaw Orthopedic, Inc., Warsaw, IN (US)

(72) Inventors: Jonathan Dewey, Memphis, TN (US); Scott Renner, Memphis, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 412 days.

(21) Appl. No.: 16/523,079

(22) Filed: Jul. 26, 2019

(65) Prior Publication Data
US 2021/0022870 A1    Jan. 28, 2021

(51) Int. Cl.
*A61F 2/46* (2006.01)
*A61F 2/30* (2006.01)
*B33Y 10/00* (2015.01)
*B33Y 80/00* (2015.01)

(52) U.S. Cl.
CPC ........ *A61F 2/30942* (2013.01); *A61F 2/4611* (2013.01); *A61F 2002/30011* (2013.01); *A61F 2002/30985* (2013.01); *B33Y 10/00* (2014.12); *B33Y 80/00* (2014.12)

(58) Field of Classification Search
CPC ......... A61F 2/4611; A61F 2002/30985; B33Y 80/00; B33Y 10/00
See application file for complete search history.

(56) References Cited

U.S. PATENT DOCUMENTS

| | | | |
|---|---|---|---|
| 8,021,138 B2 | 9/2011 | Green | |
| 8,994,592 B2 | 3/2015 | Scott et al. | |
| 9,597,730 B2 | 3/2017 | Mironets et al. | |
| 9,767,224 B2 | 9/2017 | Chou et al. | |
| 9,849,631 B1 | 12/2017 | Goss et al. | |
| 9,956,612 B1 | 5/2018 | Redding et al. | |
| 10,000,011 B1 | 6/2018 | Mark | |
| 10,010,936 B2 | 7/2018 | Chou et al. | |
| 10,011,469 B2 | 7/2018 | Craft et al. | |
| 10,022,794 B1 | 7/2018 | Redding et al. | |
| 10,022,795 B1 | 7/2018 | Redding et al. | |
| 10,029,307 B2 | 7/2018 | Shea et al. | |
| 10,035,298 B2 | 7/2018 | Mark | |
| 10,040,241 B2 | 8/2018 | Mark | |
| 10,040,242 B2 | 8/2018 | Mark | |
| 10,052,815 B2 | 8/2018 | Mark | |
| 10,406,759 B2 | 9/2019 | Loeffler et al. | |
| 2014/0065194 A1* | 3/2014 | Yoo | B29C 64/35 424/400 |
| 2016/0213485 A1* | 7/2016 | Schaufler | A61F 2/4455 |
| 2018/0326493 A1* | 11/2018 | Gallagher | B33Y 10/00 |

* cited by examiner

*Primary Examiner* — Eduardo C Robert
*Assistant Examiner* — Tara Rose E Carter

(57) ABSTRACT

A build-plate with integrally-formed spinal implant constructs and a method used in forming spinal implant constructs on the build plate and machining the spinal implant constructs formed on the build plate to manufacture spinal implants is provided. The spinal implant constructs can be formed via additive manufacturing processes by adding material to an upper surface of the build plate, and then the spinal implant constructs can be subjected to subtractive manufacturing processes to form the spinal implants.

19 Claims, 6 Drawing Sheets

BUILD-PLATE WITH INTEGRALLY-FORMED SPINAL IMPLANT CONSTRUCTS AND CORRESPONDING METHOD FOR MANUFACTURING SPINAL IMPLANTS

FIELD

The present technology is generally related to a build-plate used in forming devices such as spinal implants using additive and subtractive manufacturing processes.

BACKGROUND

Spinal implants have been formed using additive and subtractive machining processes. For example, single spinal implants have been formed by additive manufacturing processes, and thereafter, such spinal implants having been subjected to subtractive manufacturing process. The additive manufacturing processes, as their name suggests, adds material to form the spinal implants. And the subtractive manufacturing processes, as their name suggests, subtracts material to form the spinal implants. As such, the additive manufacturing processes can be used in forming general shapes of the spinal implants, and the subtractive manufacturing processes can be used in refining the shapes of the spinal implants. However, inefficiencies are created by individually forming the spinal implants by the additive manufacturing processes and then the subtractive manufacturing processes. Therefore, there is a need for an apparatus and method facilitating manufacturing of devices such as, for example, spinal implants via repeatable, batch processing for volume manufacturing using additive manufacturing processes and subtractive manufacturing processes.

SUMMARY

The techniques of this disclosure relate generally to a build-plate used in forming devices such as spinal implants using additive and subtractive manufacturing processes.

In one aspect, the present disclosure provides a method of forming a spinal implant construct on a build plate and manufacturing a spinal implant from the spinal implant construct, the method including providing the build plate having an upper surface, a first orienting surface, and a second orienting surface; forming on the upper surface of the build plate the spinal implant construct via an additive manufacturing process by adding material to the upper surface of the build plate to form the spinal implant construct at or adjacent a first end and continuing to add the material toward a second end until the spinal implant construct is formed by the additive manufacturing process; orienting the build plate relative to a subtractive-manufacturing tool using the first orienting surface, and then moving the subtractive-manufacturing tool to remove a first portion of the material from the spinal implant construct using the subtractive manufacturing tool; orienting the build plate relative to the subtractive-manufacturing tool using the second orienting surface, and then moving the subtractive-manufacturing tool to remove a second portion of the material from the spinal implant construct using the subtractive manufacturing tool; and detaching the spinal implant from the upper surface of the build plate.

In another aspect, the disclosure provides a method of forming two spinal implant constructs on a build plate and manufacturing two spinal implants from the two spinal implant constructs, the method including providing the build plate having an upper surface, a first orienting surface, and a second orienting surface; forming on the upper surface of the build plate the two spinal implant constructs each having a first end and an opposite second end via an additive manufacturing process by adding material to the upper surface of the build plate at a first location to form a first one of the spinal implant constructs at or adjacent the first end of the first one of the spinal implant constructs and continuing to add the material toward the second end of the first one of the spinal implant constructs until the first one of the two spinal implant constructs is formed by the additive manufacturing process and by adding material to the upper surface of the build plate at a second location to form a second one of the spinal implant constructs at or adjacent the first end of the second one of the spinal implant constructs and continuing to add the material toward the second end of the second one of the spinal implant constructs until the second one of the two spinal implant constructs is formed by the additive manufacturing process; orienting the build plate relative to a subtractive-manufacturing tool using the first orienting surface, and then moving the subtractive-manufacturing tool to remove a first portion of the material from each of the two spinal implant constructs using the subtractive-manufacturing tool; orienting the build plate relative to the subtractive-manufacturing tool using the second orienting surface, and then moving the subtractive-manufacturing tool to remove a second portion of the material from each of the two spinal implant constructs using the subtractive-manufacturing tool; and detaching the spinal implants from the upper surface of the build plate.

In yet another aspect, the disclosure provides a method of forming three spinal implant constructs on a build plate and manufacturing three spinal implants from the three spinal implant constructs, the method including forming on an upper surface of a build plate the three spinal implant constructs each having a first end and an opposite second end via an additive manufacturing process by adding material to the upper surface of the build plate at a first location to form a nose portion of a first one of the spinal implant constructs at or adjacent the first end of the first one of the spinal implant constructs and continuing to add the material toward the second end of the first one of the spinal implant constructs to form a first surface and a second surface of the first one of the spinal implant constructs until the first one of the three spinal implant constructs is formed by the additive manufacturing process, by adding material to the upper surface of the build plate at a second location to form a nose portion of a second one of the spinal implant constructs at or adjacent the first end of the second one of the spinal implant constructs and continuing to add the material toward the second end of the second one of the spinal implant constructs to form a first surface and a second surface of the second one of the spinal implant constructs until the second one of the three spinal implant constructs is formed by the additive manufacturing process, and by adding material to the upper surface of the build plate at a third location to form a nose portion of a third one of the spinal implant constructs at or adjacent the first end of the third one of the spinal implant constructs and continuing to add the material toward the second end of the third one of the spinal implant constructs to form a first surface and a second surface of the third one of the spinal implant constructs until the third one of the three spinal implant constructs is formed by the additive manufacturing process; orienting the build plate relative to a subtractive-manufacturing tool using a first orienting surface of the build plate, and then moving the subtractive-manufacturing tool to remove a first portion of the material from each of the three spinal implant constructs; orienting the build plate relative to the subtractive-manufacturing tool using a second orienting surface of the build plate, and then moving the subtractive-manufacturing tool to remove a second portion of the material from each of the three spinal implant constructs; orienting the build plate relative to the subtractive-manufacturing tool using a third orienting surface of the build plate, and then moving the subtractive-manufacturing tool to remove a third portion of the material from each of the three spinal implant constructs; and detaching each of the spinal implants from the upper surface of the build plate.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
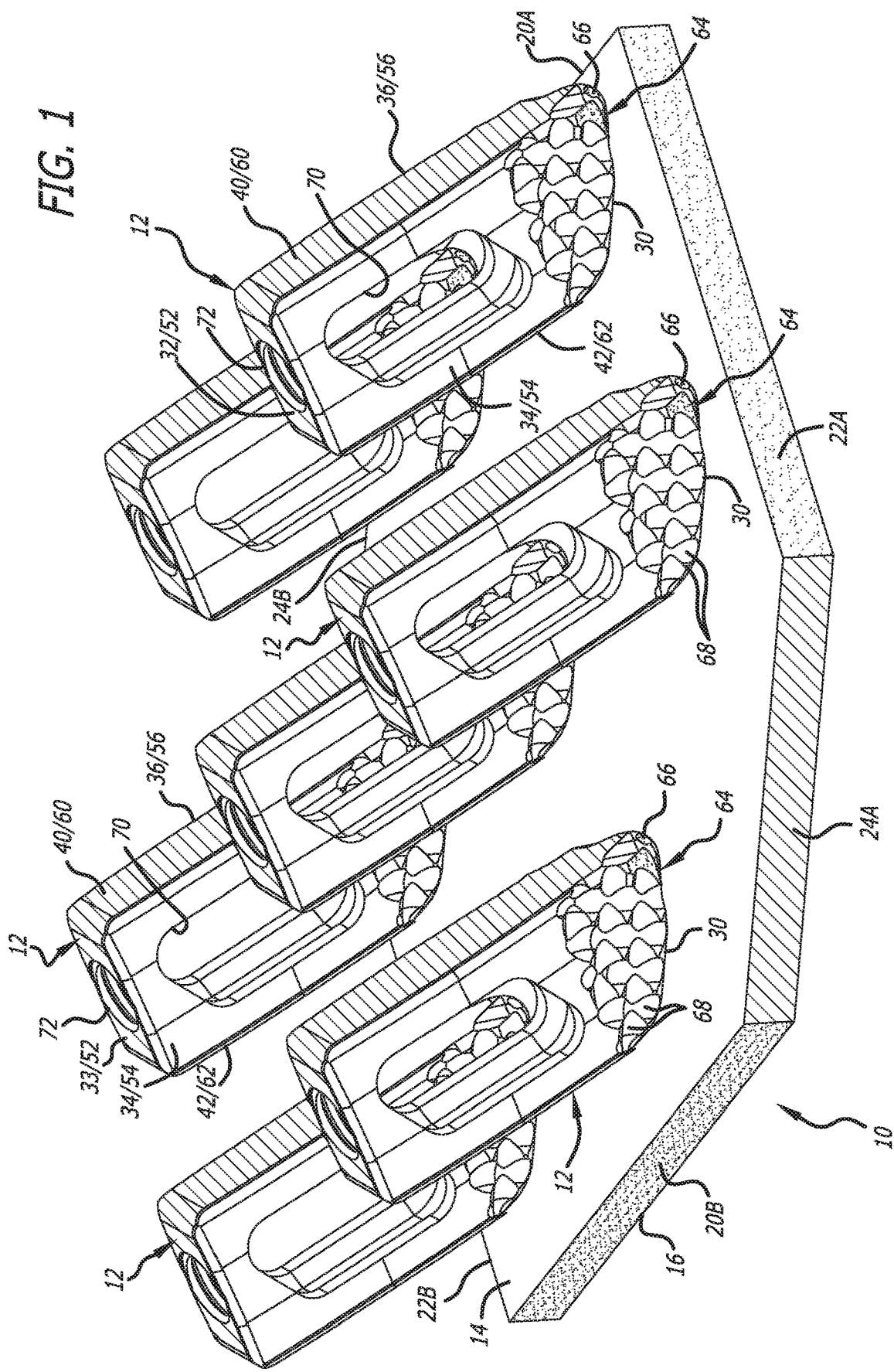
FIG. 1 is a top, side, perspective view that illustrates a build-plate with various spinal implant constructs formed on the build-plate.
Figure 2:
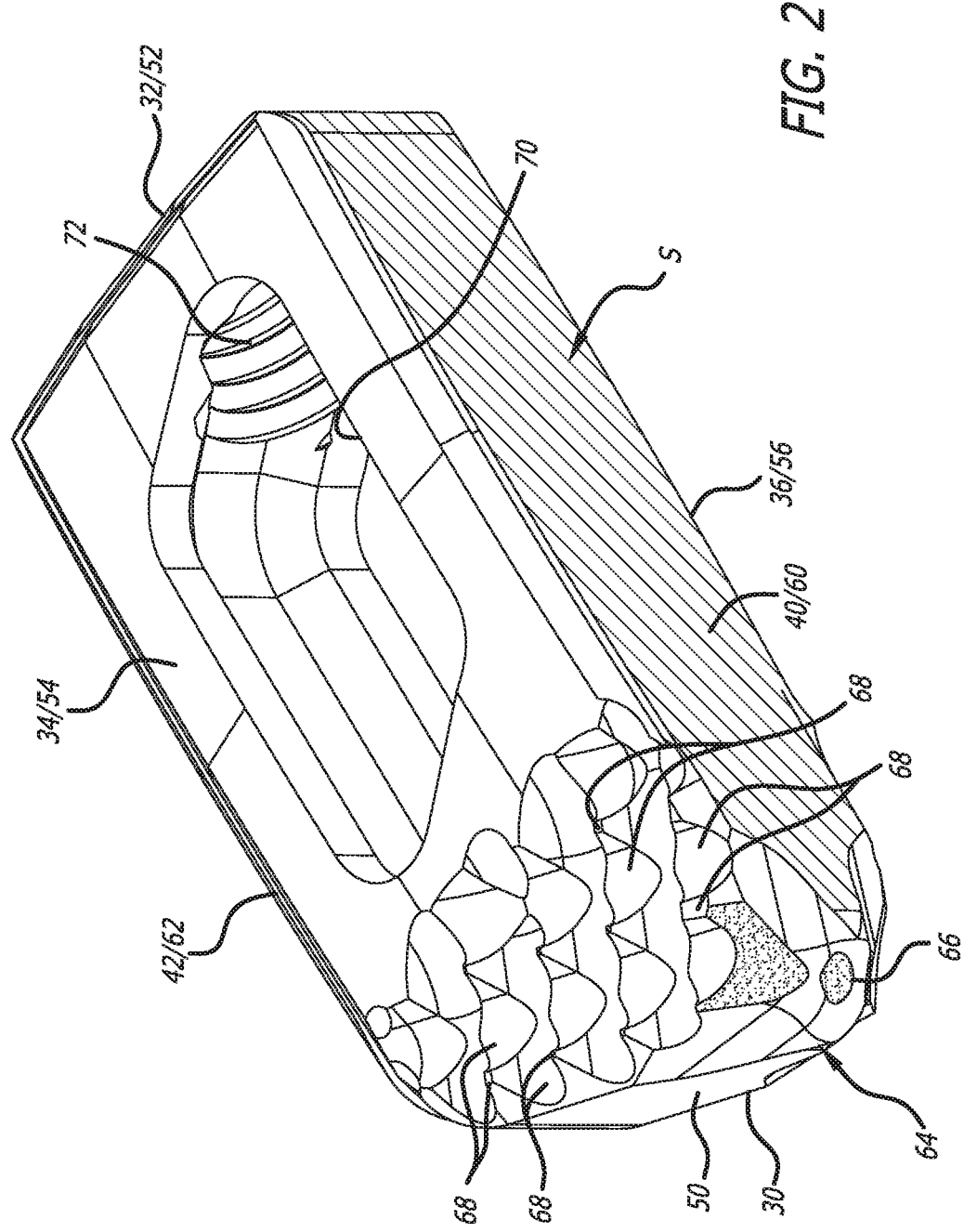
FIG. 2 is a top, side, perspective view that illustrates a spinal implant formed from one of the spinal implant constructs of FIG. 1.

An additive build-plate according to a preferred embodiment of the present disclosure is generally indicated by the numeral 10 in FIGS. 1 and 3-5. Initially, the build-plate 10 is used to afford formation of one or more constructs on the build-plate 10 via additive manufacturing (or machining) processes such as, for example, a 3D printing process. To illustrate, the one or more constructs formed on the build-plate 10 can be spinal implant constructs 12 used to form surgical implants such as spinal implants S (FIG. 2). The spinal implants S can be used for spinal fusion via insertion into a disc space between adjacent vertebral bodies.

As discussed below, the spinal implant constructs 12 are formed on a surface of the build-plate 10 such that, after formation of the spinal implant constructs 12, the spinal implant constructs 12 can be further manufactured using additional manufacturing processes to facilitate completion of the manufacture of the spinal implants S. Such additional manufacturing processes can be used to change the geometry or the surfaces of the spinal implant constructs 12, and the additional manufacturing processes can include subtractive manufacturing (or machining) processes.

The build-plate 10 with the spinal implant constructs 12 can serve as a unitary workpiece facilitating additional manufacturing processes (such as the subtractive manufacturing processes) applied thereto to manufacture the spinal implants S. The build-plate 10 with the spinal implant constructs 12 can be used to facilitate repeatable, batch processing for volume manufacturing of the spinal implants S using additive manufacturing processes and subtractive manufacturing processes. Furthermore, the spinal implant constructs 12 can be formed of materials compatible with additive manufacturing processes and/or subtractive manufacturing processes including, but not limited to, metals, polymers, and ceramics.

As discussed below, the spinal implant constructs 12 can be formed (or grown) using an additive manufacturing process or processes, and then be subjected to a subtractive manufacturing process or processes to complete manufacture of the spinal implants S. However, the manufacturing of the spinal implants S using the build-plate 10 is not so limited. Additional serial or alternating additive manufacturing processes and subtractive manufacturing processes can be used to facilitate completion of the manufacture of the spinal implants S. For example, the additive manufacturing processes are often used to create roughened surfaces, and the subtractive manufacturing process are often used to create smoothened surfaces. When the spinal implant S are used as spinal fusion implants, the roughened surfaces can be useful in promoting bone ingrowth, and the smoothed surfaces can be useful in facilitating insertion into the disc space. Thus, the additive manufacturing processes and the subtractive manufacturing process can be used to create surfaces on the spinal implants S according to the desired use of the surfaces.

The build-plate 10 can have various shapes, and includes an upper surface 14, a lower surface 16, and various side surfaces between the upper surface 14 and the lower surface 16. The build-plate 10 can include three (3) or more side surfaces, and the number of side surfaces can determine the shape of the upper surface 14 and the lower surface 16. As depicted in FIG. 1, the build-plate 10 includes six (6) side surfaces, and the upper surface 14 and the lower surface 16 are correspondingly formed as hexagons. The six (6) side surfaces include first opposed sides 20A and 20B, second opposed sides 22A and 22B, and third opposed sides 24A and 24B.

Each of the sets of opposed sides can have various known geometric orientations with respect to the other sets of opposed sides. As depicted in FIG. 1, each of the sets of opposed sides can be parallel to one another, and the set of the first opposed sides 20A and 20B and the set of the second opposite sides 22A and 22B can be approximately oriented perpendicularly with respect to one another, and the sets of the first opposed sides 20A and 20B and the second opposed sides 22A and 22B can be approximately oriented 135° with respect to the set of the third opposed sides 24A and 24B. Using their known geometric orientations, the various side surfaces can be used to facilitate positioning of the build-plate 10 to facilitate both of the additive and subtractive manufacturing processes.

Additionally, one or more of the first opposed sides 20A and 20B, the second opposed sides 22A and 22B, and the third opposed sides 24A and 24B can include setup orientation features. The setup orientation features can include colors, textures, letters, numbers, markings (with embossed and/or recessed text, and/or embossed and/or recessed markings such as, for example, circles, rectangles, triangles, star, etc.) to facilitate positioning of the build-plate 10. For example, as depicted FIGS. 1 and 3-5, the first opposed sides 20A and 20B can include a first setup orientation feature in the form of a first color or texture as indicated by a first type of stippling, the second opposed side 22A can include a second setup orientation feature in the form of a second color or texture as indicated by a second type of stippling, and the third opposed sides 24A and 24B can include a third setup orientation feature in the form of a third color or texture as indicated by cross-hatching. Although not shown in FIGS. 1 and 3-5, the second opposed side 22B can also include the second setup orientation feature in the form of the second color or texture. Using their known color and/or textures, the various side surfaces can be used to facilitate positioning of the build-plate 10 to facilitate both of the additive and subtractive manufacturing processes.

As discussed below, the geometric orientations and/or the setup orientation features of the first opposed sides 20A and 20B, the second opposed sides 22A and 22B, and the third opposed sides 24A and 24B can be scanned by one or more laser or optical scanners (not shown) to determine the position of the build-plate 10 and to afford corresponding adjustments (if necessary).

As discussed above, the spinal implant constructs 12 or other constructs can be formed on the upper surface 14. The spinal implant constructs 12 and the spinal implants S formed from the spinal implant constructs 12, as depicted in FIGS. 1-5, can each include a first end 30, an opposite second end 32, opposed first and second sides 34 and 36, and opposed third and fourth sides 40 and 42. The first side 34, the second side 36, the third side 40, and the fourth side 42 of each of the spinal implant constructs 12 and the spinal implants S extend between the first end 30 and the second end 32. Furthermore, as depicted in FIGS. 1-5, each of the spinal implant constructs 12 and the spinal implants S can include a leading end surface 50 formed at and adjacent the first end 30, a trailing end surface 52 formed at the second end 32, a first surface 54 on the first side 34, a second surface 56 on the second side 36, a first side surface 60 at the third side 40, and a second side surface 62 at the fourth side 42. As discussed below, the leading end surfaces 50 are ultimately where each of the spinal implant constructs 12 are separated from the upper surface 14 of the build-plate 10 to form the spinal implants S.

The spinal implant constructs 12 and the spinal implants S can each include a nose portion 64 terminating at a tip portion 66 at and adjacent the first end 30. The nose portion 64 can be formed from portions of the leading end surface 50, the first surface 54, the second surface 56, and the first side surface 60. As depicted in FIGS. 1-3 and 5, the nose portion 64 can be wedge-shaped, and to form the wedge shape of nose portion 64, portions of each of the leading end surface 50 and the first side surface 60 truncate toward the first end 30, and the portions of the first surface 54 and the second surface 56 slope toward the first end 30. The configurations of the nose portion 64 and the tip portion 66 are used during spinal surgery to facilitate entry of the spinal implant S into position in a disc space between adjacent vertebral bodies. Furthermore, one of the first surface 54 and the second surface 56 can be the upper surface of the spinal implant S for contacting an endplate of an upper one of the adjacent vertebral bodies, and the other of the first surface 54 and the second surface 56 can be the lower surface of the spinal implant S for contacting an endplate of a lower one of the adjacent vertebral bodies.

Additionally, the spinal implant constructs 12 and the spinal implants S can each include depressions and projections 68 formed on the first surface 54 and the second surface 56, an aperture 70 extending between the first surface 54 and the second surface 56, a tool-engaging aperture 72 formed through the trailing end surface 52. One of the first surface 54 and the second surface 56 can be the upper surface of the spinal implant S, and the other of the first surface 54 and the second surface 56 can be the lower surface of the spinal implant S. The depressions and projections 68 can be used for contacting the endplates of the adjacent vertebral bodies and facilitating bone ingrowth to maintain the position of the spinal implant S in the disc space. Furthermore, the aperture 70 can be used to facilitate bone growth through the spinal implant S between an upper one and a lower one of the adjacent vertebral bodies. And the tool-engaging aperture 72 can be used for attaching the spinal implant S to an insertion instrument (not shown) to facilitate inserting the spinal implant S into position in the disc space.

For each of the spinal implant constructs 12, an additive manufacturing process can begin by positioning the build-plate 10 relative to an additive manufacturing platform or machine (not shown) for effectuating the additive manufacturing process. The known geometric orientations and/or the setup orientation features of at least one of the various sides of the build-plate 10 can be scanned by the one or more laser or optical scanners to determine the position of the build-plate 10 to afford positional adjustment (if necessary) of the build-plate 10 relative to the additive manufacturing platform to facilitate properly orienting of the spinal implant constructs 12 to be formed on the build-plate 10. Thereafter, material can be added by the additive manufacturing machine to the upper surface 14 of the build-plate 10 to form a portion of the spinal implant construct 12 at and/or adjacent the first end 30 and material can be continually added by the additive manufacturing platform toward the second end 32 until the spinal implant construct 12 is formed by the additive manufacturing process. The additive manufacturing process is repeated to form each of the spinal implant constructs 12 on the build-plate 10. Although the spinal implants constructs 12 discussed as being grown first at or adjacent the first end 30 and then grown toward the second end 32, the formation of the spinal implant constructs 12 is not so limited. The spinal implant constructs 12 could be grown in any number of orientations with respect to the build-plate 10. Furthermore, the additive manufacturing platform used for forming the spinal implant constructs 12 on the build-plate 10 can include, but is not limited to, a 3D printer for effectuating 3D printing processes such as, for example, powder bed fusion.

Thereafter, a subtractive manufacturing process begins by positioning the build-plate 10 relative to a subtractive manufacturing platform or machine (not shown). The known geometric orientations and/or the setup orientation features of at least one of the various sides of the build-plate 10 can be scanned by the one or more laser or optical scanners to determine the position of the build-plate 10 to properly orient the spinal implant constructs 12 formed the build-plate 10 relative to the subtractive manufacturing platform. Thereafter, the subtractive manufacturing platform is used to effectuate the subtractive manufacturing process to remove material from the spinal implant constructs 12. The subtractive manufacturing platform used to remove material from the spinal implant constructs can include, but is not limited to, machines for electrical discharge machining (EDM), CNC machining (turning, drilling boring, milling, reaming, etc.), laser cutting/etching, and water jet cutting/etching.

The known geometric orientations and/or the setup orientation features of at least one of the various sides of the build-plate 10, and the identical orientations of the spinal implant constructs 12 formed on the build-plate 10 eases use of the subtractive manufacturing processes by affording accurate and repeatable movement of a tool (not shown) of the subtractive manufacturing platform performing the subtractive manufacturing process. Accurate positioning of the build-plate 10 and the subtractive-manufacturing tool relative to one another affords accurate and duplicative movement of the tool to machine the spinal implant constructs 12 formed on the build-plate 10. The one or more laser or optical scanners can be used repeatedly to provide updates on the position of the build-plate 10 to insure continued proper movement of the tool as the build-plate 10 is oriented or reoriented during the subtractive manufacturing processes.

Relative movement of the build-plate 10 and the subtractive-manufacturing tool with respect one another allows the tool to movement in one or more predefined pathways to remove material from the build-plate 10 and/or the spinal implant constructs 12. For example, at least one of the first opposed sides 20A and 20B of the build-plate 10 can be used to align the build-plate 10 in a first orientation on a machining platform (not shown) located with respect to the tool of the subtractive manufacturing platform. Then, the tool performing subtractive manufacturing process can be moved in accurate and repeatable motions relative to the spinal implant constructs 12 formed on the build-plate 10 to remove material, and/or the build-plate 10 can be moved by the machining platform in accurate and repeatable motions relative to the tool performing the subtractive manufacturing process to remove material. After completion of the subtractive manufacturing process with the build-plate 10 in the first orientation, the build-plate 10 can be aligned in a second orientation (using one of the second opposed side surfaces 22A and 22B to facilitate alignment) and then a third orientation (using one of the third opposed side surfaces 24A and 24B to facilitate alignment) relative to the machining platform. When in either of the second orientation or the third orientation, the tool can be moved in accurate and repeatable motions relative to the spinal implant constructs 12, and/or the build-plate 10 can be moved by the machining platform in accurate and repeatable motions relative to the tool to facilitate the subtractive manufacturing processes in these orientations.

Figure 3:
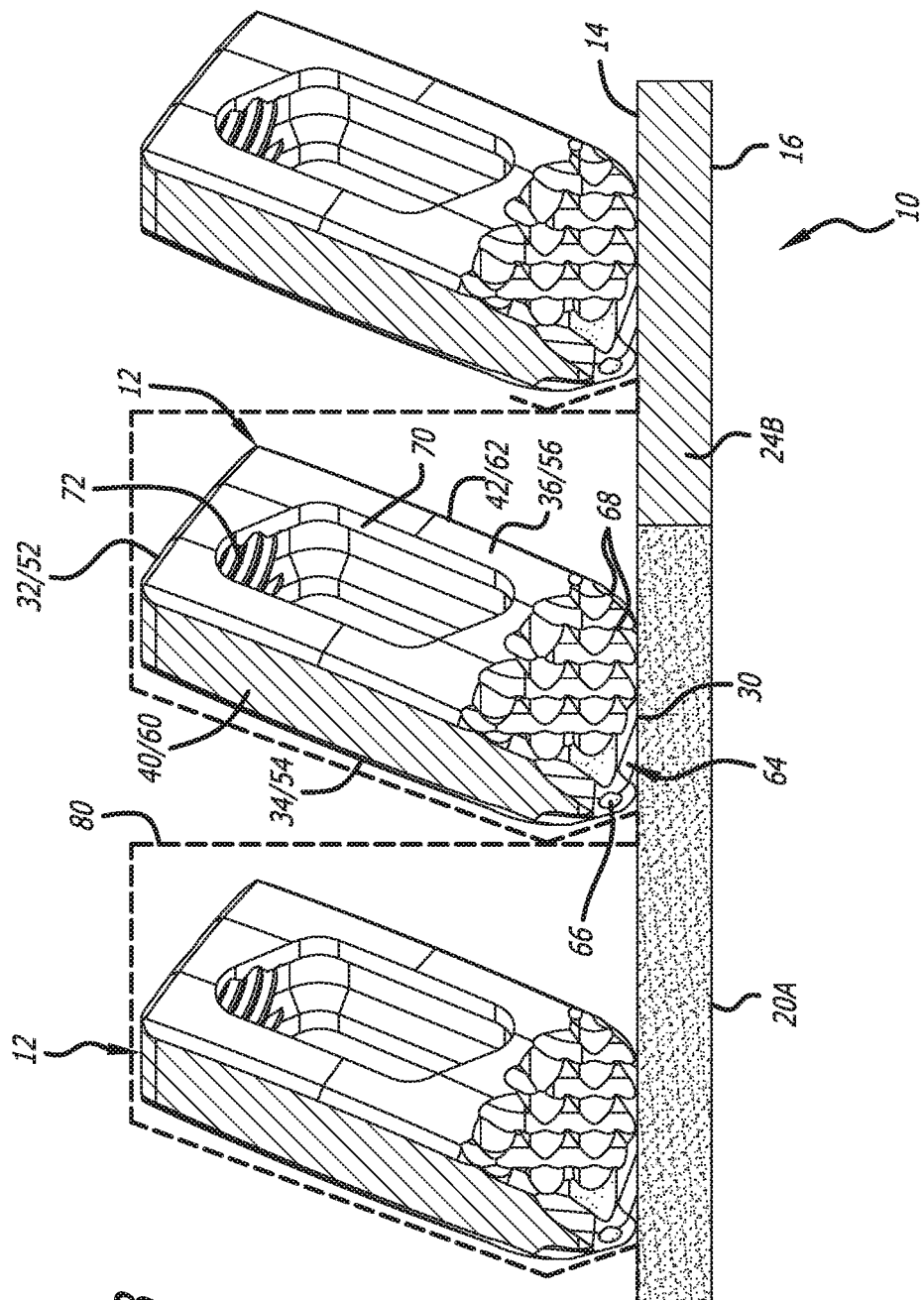
FIG. 3 is a first, side elevational view that illustrates the build-plate of FIG. 1 with the various spinal implant constructs formed on the build-plate, and a first path of a subtractive-machining tool for subtractively machining the spinal implant constructs.
Figure 4:
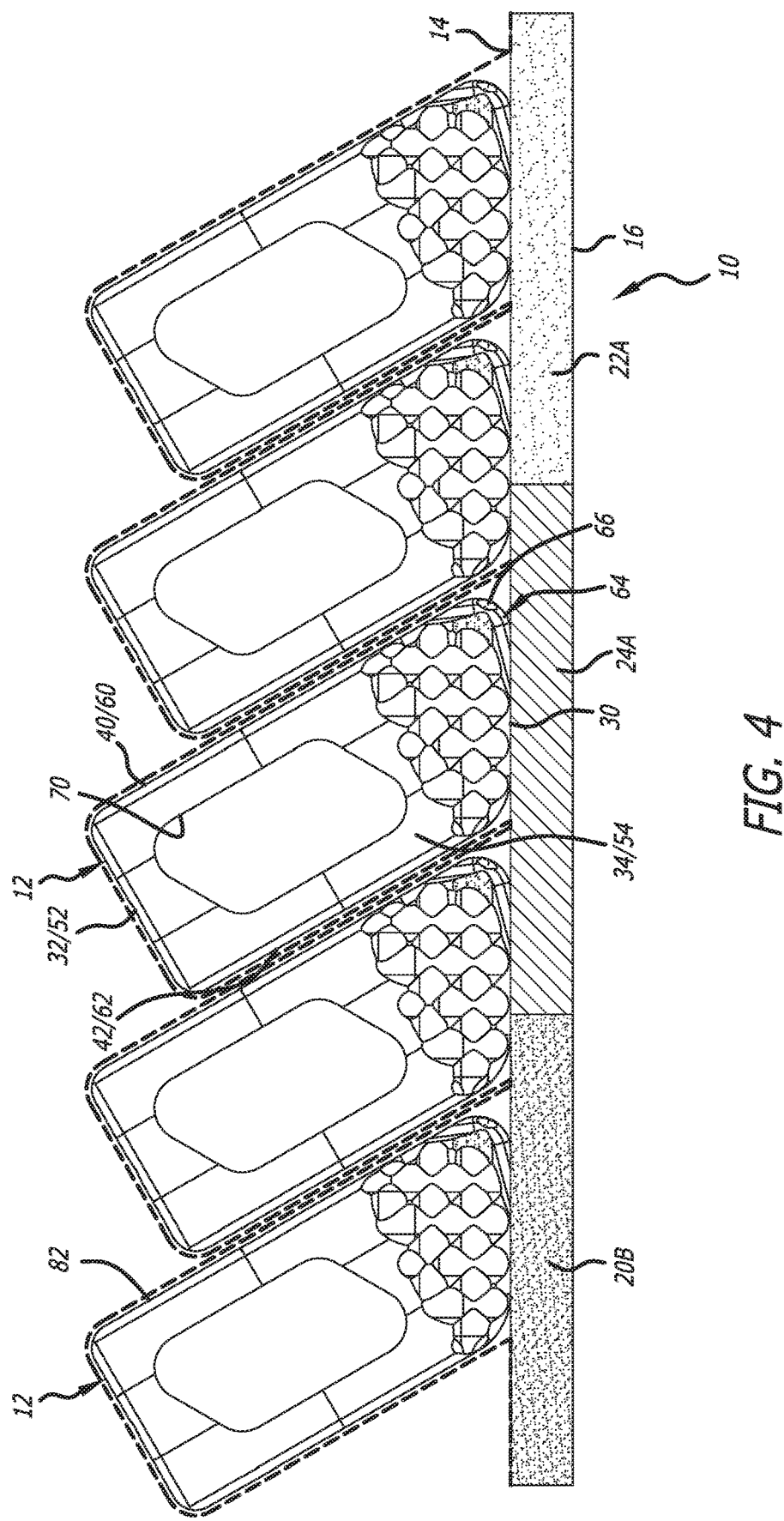
FIG. 4 is a second, side elevational view that illustrates the build-plate of FIG. 1 with the various spinal implant constructs formed on the build-plate, and a second path of the subtractive-machining tool for subtractively machining the spinal implant constructs.
Figure 5:
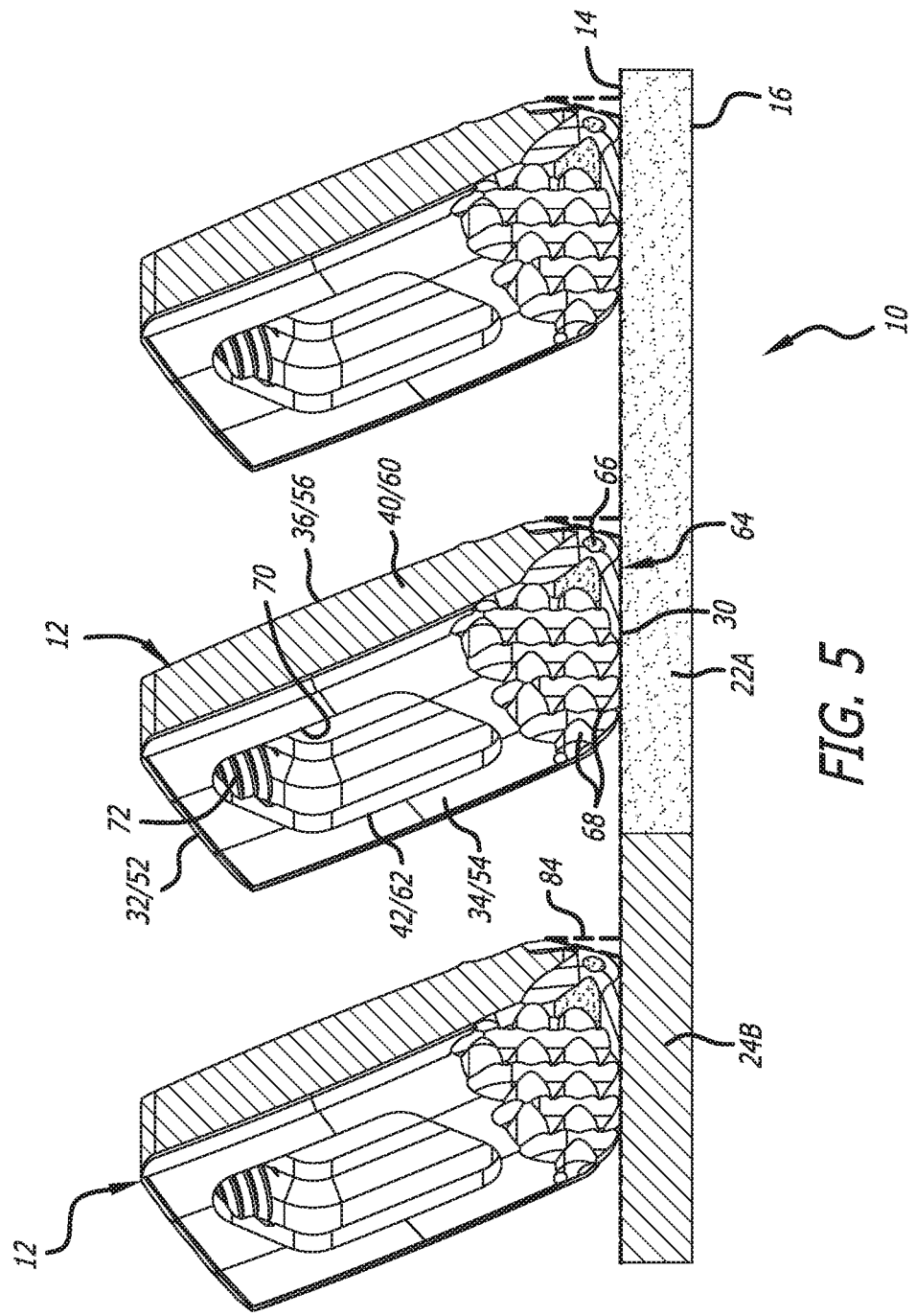
FIG. 5 is a third, side elevational view that illustrates the build-plate of FIG. 1 with the various spinal implant constructs formed on the build-plate, and a third path of the subtractive-machining tool for subtractively machining the spinal implant constructs.

To illustrate, when using an EDM process, the build-plate 10 can be aligned relative to the subtractive manufacturing platform using one of the first opposed side surfaces 20A and 20B, and a wire (not shown) of the EDM tool can be moved along a first pathway 80 depicted in FIG. 3. As depicted in FIG. 4, the build-plate 10 can also be aligned relative to the subtractive manufacturing platform using one of the third opposed side surfaces 24A and 24B, and the wire of the EDM tool can be moved along a second pathway 82. Furthermore, as depicted in FIG. 5, the build-plate 10 can also be aligned relative to the subtractive manufacturing platform using one of the second opposed side surfaces 22A and 22B, and the wire of the EDM tool can be moved along a third pathway 84. The first pathway 80, the second pathway 82, and the third pathway 84 are illustrated as bold and dashed lines for clarity.

For example, using the first pathway 80, the wire of the EDM tool can be used to shape and/or smoothen one side of the nose portion 64 and/or the tip portion 66; using the second pathway 82, the wire of the EDM tool can be used to shape and/or smoothen portions of the trailing end surface 52, the first side surface 60, and the second side surface 62 of the spinal implant constructs 12; and using the third pathway 84, the wire of the EDM tool can be used to shape and/or smoothen the other side of the nose portion 64 and/or the tip portion 66 and to cut away the spinal implant constructs 12 from the build-plate 10 along what becomes the leading end surfaces 50 of the spinal implants S. The tool performing the subtractive manufacturing process can be moved in repeatable motions according to the first pathway 80, the second pathway 82, and the third pathway 84 relative to the spinal implant constructs 12 formed on the build-plate 10 to remove material, and/or the build-plate 10 can be moved by the machining platform in repeatable motions relative to the tool performing the EDM process according to the first pathway 80, the second pathway 82, and the third pathway 84 to remove material. Furthermore, the tool performing the subtractive manufacturing process can be oriented, as needed, at different angles with respect to the first opposed side surfaces 20A and 20B, the second opposed side surfaces 22A and 22B, the third opposed side surfaces 24A and 24B, and the wire of the EDM tool can be moved along a second pathway 82.

The first pathway 80, the second pathway 82, and the third pathway 84 are illustrative of pathways used to remove materials from the spinal implant constructs 12. One or more pathways of the subtractive-manufacturing tool can also be used to remove material from the spinal implant constructs 12. These one or more pathways can be selectively chosen to provide different finishes to different parts of the spinal implant constructs 12. For example, material can be removed from the spinal implant constructs 12 via the one or more pathways to shape and/or smoothen the first surface 54 and the second surface 56, and/or material can also be removed from the spinal implant constructs 12 to form chamfers at the intersections of the various surfaces (i.e., the trailing end surface 52, the first surface 54, the second surface 56, the first side surface 60, or the second side surface 62) of the spinal implant constructs 12. One or more pathways of the subtractive-manufacturing tool can also be used in separating the spinal constructs 12 from the build-plate 10 to form the spinal implants S. For example, material can be removed from the build-plate 10 and/or spinal implant constructs 12 by the subtractive-manufacturing tool to form one or more detachment areas between the build-plate 10 and/or the spinal implant constructs 12. The detachment areas facilitate separation of the spinal implant constructs 12 to the build-plate 10 to form the spinal implants S. Furthermore, detachment areas of the spinal implant constructs 12 can ultimately form leading surfaces such as the leading end surface 50 of each of the spinal implants S.

Figure 6:
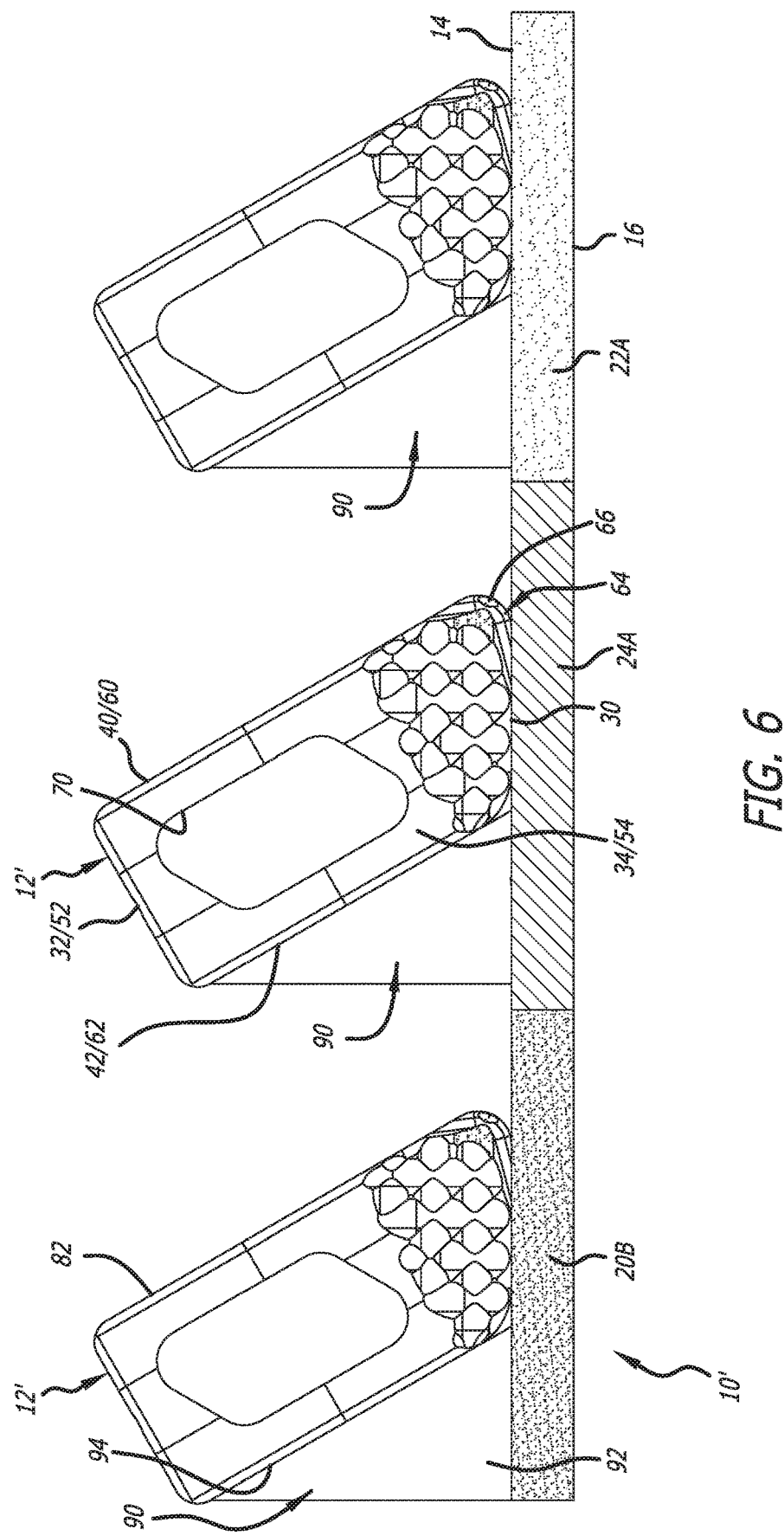
FIG. 6 is side elevational view that illustrates a modified build-plate with various spinal implant constructs formed on the build-plate with each of the spinal implant constructs being supported on the build-plate by supports that can ultimately be removed by subtracting machining the supports.

Additionally, FIG. 6 depicts another elevational view that illustrates a build-plate 10' with various spinal implant constructs 12'. As indicated by the identical numbering applied in FIG. 6, the build-plate 10' can include identical or similar features as the build-plate 10, and the spinal implant constructs 12' can be formed identically or similarly to the spinal implant constructs 12'. As depicted in FIG. 6, each of the spinal implant constructs 12' can be formed with and supported by a support 90. Each of the supports 90 includes a first portion 92 attached to the build-plate 10' and a second portion 94 attached to one of the spinal implant constructs 12'. The remainders of each of the support 90 serves as a web that facilitates support of the spinal implant constructs 12' on the build-plate 10. The supports 90 can be removed during the subtractive manufacturing processes using, for example, one or more pathways of the EDM tool. To illustrate, removal of the supports 90 can be effectuated using the first pathway 80, the second pathway 82, and the third pathway 84.

While the spinal implant constructs 12 are formed on the build-plate 10, the present disclosure is not so limited. Other devices can be formed on the build-plate 10 using the above-discussed additive manufacture processes, and then machined using the above-discussed subtractive manufacturing processes.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method of forming a spinal implant construct on a build plate and manufacturing a spinal implant from the spinal implant construct, the method comprising:
    providing the build plate having an upper surface, a first orienting surface, and a second orienting surface;
    forming on the upper surface of the build plate the spinal implant construct via an additive manufacturing process by adding material to the upper surface of the build plate to form the spinal implant construct at or adjacent a first end and continuing to add the material toward a second end until the spinal implant construct is formed by the additive manufacturing process;
    orienting the build plate relative to a subtractive-manufacturing tool using the first orienting surface, and then via relative movement of the subtractive-manufacturing tool and the build plate, removing a first portion of the material from the spinal implant construct using the subtractive manufacturing tool;
    orienting the build plate relative to the subtractive-manufacturing tool using the second orienting surface, and then via relative movement of the subtractive-manufacturing tool and the build plate, removing a second portion of the material from the spinal implant construct using the subtractive manufacturing tool;
    forming a detachment area between the build-plate and the spinal implant construct via a subtractive manufacturing process, wherein the spinal implant is detached from the build plate at the detachment area, and the detachment area forms a leading surface of the spinal implant; and
    detaching the spinal implant from the upper surface of the build plate.

2. The method of claim 1, wherein forming the spinal implant construct includes forming a nose portion of the spinal implant construct at or adjacent the first end of the spinal implant construct, and forming a first surface and a second surface that extend from at or adjacent the first end toward the second end.

3. The method of claim 2, wherein one of the first surface and the second surface of the spinal implant construct forms an upper surface of the spinal implant, and the other of the first surface and the second surface of the spinal implant construct forms a lower surface of the spinal implant.

4. The method of claim 3, wherein forming the spinal implant construct includes forming an aperture between the first surface and the second surface.

5. The method of claim 2, wherein the relative movement of the subtractive-manufacturing tool and the build-plate removes the first portion of the material occurs along a first path, and the relative movement of the subtractive-manufacturing tool and the build-plate removes the second portion of the material occurs along a second path.

6. The method of claim 5, wherein, during the relative movement along one of the first path and the second path, the subtractive-manufacturing tool removes the first portion of the material from the nose portion to shape and/or smoothen the nose portion.

7. The method of claim 6, wherein, during the relative movement along the other of the first path and the second path, the subtractive-manufacturing tool removes the second portion of the material from one of the first surface and the second surface to shape and/or smoothen the one of the first surface and the second surface.

8. A method of forming two spinal implant constructs on a build plate and manufacturing two spinal implants from the two spinal implant constructs, the method comprising:
    providing the build plate having an upper surface, a first orienting surface, and a second orienting surface;
    forming on the upper surface of the build plate the two spinal implant constructs each having a first end and an opposite second end via an additive manufacturing process by adding material to the upper surface of the build plate at a first location to form a first one of the spinal implant constructs at or adjacent the first end of the first one of the spinal implant constructs and continuing to add the material toward the second end of the first one of the spinal implant constructs until the first one of the two spinal implant constructs is formed by the additive manufacturing process and by adding material to the upper surface of the build plate at a second location to form a second one of the spinal implant constructs at or adjacent the first end of the second one of the spinal implant constructs and continuing to add the material toward the second end of the second one of the spinal implant constructs until the second one of the two spinal implant constructs is formed by the additive manufacturing process;
    orienting the build plate relative to a subtractive-manufacturing tool using the first orienting surface, and then via relative movement of the subtractive-manufacturing tool and the build plate, removing a first portion of the material from each of the two spinal implant constructs using the subtractive-manufacturing tool;
    orienting the build plate relative to the subtractive-manufacturing tool using the second orienting surface, and then via relative movement of the subtractive-manufacturing tool and the build plate, removing a second portion of the material from each of the two spinal implant constructs using the subtractive-manufacturing tool; and
    detaching the spinal implants from the upper surface of the build plate.

9. The method of claim 7, further comprising forming detachment areas between the build plate and the two spinal implant constructs via a subtractive manufacturing process, wherein the two spinal implants are detached from the build plate at the detachment areas, and the detachment areas form leading surfaces of the two spinal implants.

10. The method of claim 8, wherein forming the two spinal implant constructs includes forming a nose portion of each of the two spinal implant constructs at or adjacent each of the first ends of the two spinal implant constructs, and forming a first surface and a second surface that extend from at or adjacent each of the first ends toward each of the second ends.

11. The method of claim 10, wherein one of the first surface and the second surface of each of the two spinal implant constructs forms an upper surface of each of the two spinal implants, and the other of the first surface and the second surface of each of the two spinal implant constructs forms a lower surface of the spinal implant.

12. The method of claim 11, wherein forming the two spinal implant constructs includes forming an aperture between the first surface and the second surface of each of the first one and the second one of the two spinal implant constructs.

13. The method of claim 10, wherein the relative movement of the subtractive-manufacturing tool and the build plate removes the first portions of the material from each of the two spinal implant constructs occurs along a first path, and the relative movement along the first path removes the first portions of the material from the nose portion of each of the two spinal implant constructs to shape and/or smoothen the nose portion of each of the two spinal implant constructs.

14. The method of claim 13, wherein the relative movement of the subtractive-manufacturing tool and build plate removes the second portions of the material from each of the two spinal implant constructs occurs along a second path, and the relative movement along the second path removes the second portions of the material from one of the first surface and the second surface of each of the two spinal implant constructs to shape and/or smoothen the one of the first surface and the second surface of each of the two spinal implant constructs.

15. The method of claim 14, wherein forming the two spinal implant constructs includes forming a third surface and a fourth surface of each of the two spinal implant constructs, and further comprising removing, via relative movement of the subtractive-manufacturing tool and the build plate along a third path, a third portion of the material from one of the third surface and the fourth surface of each of the two spinal implant constructs to shape and/or smoothen the one of the third surface and the fourth surface.

16. A method of forming three spinal implant constructs on a build plate and manufacturing three spinal implants from the three spinal implant constructs, the method comprising:
    forming on an upper surface of a build plate the three spinal implant constructs each having a first end and an opposite second end via an additive manufacturing process by adding material to the upper surface of the build plate at a first location to form a nose portion of a first one of the spinal implant constructs at or adjacent the first end of the first one of the spinal implant constructs and continuing to add the material toward the second end of the first one of the spinal implant constructs to form a first surface and a second surface of the first one of the spinal implant constructs until the first one of the three spinal implant constructs is formed by the additive manufacturing process, by adding material to the upper surface of the build plate at a second location to form a nose portion of a second one of the spinal implant constructs at or adjacent the first end of the second one of the spinal implant constructs and continuing to add the material toward the second end of the second one of the spinal implant constructs to form a first surface and a second surface of the second one of the spinal implant constructs until the second one of the three spinal implant constructs is formed by the additive manufacturing process, and by adding material to the upper surface of the build plate at a third location to form a nose portion of a third one of the spinal implant constructs at or adjacent the first end of the third one of the spinal implant constructs and continuing to add the material toward the second end of the third one of the spinal implant constructs to form a first surface and a second surface of the third one of the spinal implant constructs until the third one of the three spinal implant constructs is formed by the additive manufacturing process;
    orienting the build plate relative to a subtractive-manufacturing tool using a first orienting surface of the build plate, and then via relative movement of the subtractive manufacturing tool and the build plate, removing a first portion of the material from each of the three spinal implant constructs;
    orienting the build plate relative to the subtractive-manufacturing tool using a second orienting surface of the build plate, and then via relative movement of the subtractive manufacturing tool and the build plate, removing a second portion of the material from each of the three spinal implant constructs;
    orienting the build plate relative to the subtractive-manufacturing tool using a third orienting surface of the build plate, and then via relative movement of the subtractive manufacturing tool and the build plate, removing a third portion of the material from each of the three spinal implant constructs; and
    detaching each of the spinal implants from the upper surface of the build plate.

17. The method of claim 16, further comprising forming detachment areas between the build plate and the three spinal implant constructs via a subtractive manufacturing process, wherein the three spinal implants are detached from the build plate at the detachment areas, and the detachment areas form leading surfaces of the three spinal implants.

18. The method of claim 16, wherein the relative movement of the subtractive-manufacturing tool and the build-plate occurs along a first path to remove the first portions of the material from the nose portion of each of the three spinal implant constructs to shape and/or smoothen the first portion of the nose portion of each of the three spinal implant constructs.

19. The method of claim 18, wherein the relative movement of the subtractive-manufacturing tool and the build-plate occurs along a second path to remove the second portions of the material from one of the first surface and the second surface of each of the three spinal implant constructs to shape and/or smoothen the one of the first surface and the second surface of each of the three spinal implant constructs.

* * * * *